US010442028B2

(12) United States Patent
Dunbar et al.

(10) Patent No.: US 10,442,028 B2
(45) Date of Patent: *Oct. 15, 2019

(54) WELDING HELMET CONFIGURATION PROVIDING REAL-TIME FUME EXPOSURE WARNING CAPABILITY

(71) Applicant: Lincoln Global, Inc., Santa Fe Springs, CA (US)

(72) Inventors: Douglas N. Dunbar, Strongsville, OH (US); Bruce John Chantry, Solon, OH (US); Badri K. Narayanan, Highland Hts., OH (US); Steven R. Sumner, Brunswick, OH (US); William T. Matthews, Chesterland, OH (US)

(73) Assignee: LINCOLN GLOBAL, INC., Santa Fe Springs, CA (US)

(*) Notice: Subject to any disclaimer, the term of this patent is extended or adjusted under 35 U.S.C. 154(b) by 254 days.

This patent is subject to a terminal disclaimer.

(21) Appl. No.: 15/665,554

(22) Filed: Aug. 1, 2017

(65) Prior Publication Data

US 2017/0326674 A1     Nov. 16, 2017

Related U.S. Application Data

(63) Continuation-in-part of application No. 15/281,784, filed on Sep. 30, 2016, now Pat. No. 9,750,295, which
(Continued)

(51) Int. Cl.
*B23K 9/32* (2006.01)
*G08B 21/12* (2006.01)
(Continued)

(52) U.S. Cl.
CPC ............. *B23K 9/322* (2013.01); *A42B 3/046* (2013.01); *A61F 9/06* (2013.01); *A61F 9/068* (2013.01); *G08B 21/12* (2013.01)

(58) Field of Classification Search
CPC combination set(s) only.
See application file for complete search history.

(56) References Cited

U.S. PATENT DOCUMENTS 3,814,552 A   6/1974  Guggenheim
4,195,363 A   4/1980  Jenson
(Continued)

FOREIGN PATENT DOCUMENTS

CA    2038252 A1    9/1992
CN    205108059 U   3/2016
(Continued)

OTHER PUBLICATIONS

Text of the Office Action issued by the Japanese Patent Office dated Nov. 22, 2016 in related Japanese pending Patent application 2015-237565.
(Continued)

*Primary Examiner* — Nabil H Syed
*Assistant Examiner* — Cal J Eustaquio
(74) *Attorney, Agent, or Firm* — Brad C. Spencer (57) ABSTRACT

Welding helmets, systems, and kits providing real-time fume exposure monitoring and warning capability during an arc welding process. A welding helmet configured to protect the head of a user during a welding process is configured with an intelligent warning apparatus and an air-sampling pick-up and output port. The air-sampling pickup and output port connects to a proximal end of an air sampling tube for sampling breathable air within the welding helmet, and a distal end of the air-sampling tube connects to an air-sampling in-take port of an external aerosol monitoring device. The intelligent warning apparatus communicates with the aerosol monitoring device to receive air sample output data from the aerosol monitoring device, and to process the air sample output data to generate warning data
(Continued)

and/or warning signals based on preset exposure level set points and/or exposure warning operating modes.

20 Claims, 6 Drawing Sheets

Related U.S. Application Data is a continuation-in-part of application No. 13/106,525, filed on May 12, 2011, now abandoned.

(51) Int. Cl.
*A42B 3/04* (2006.01)
*A61F 9/06* (2006.01)

(56) References Cited

U.S. PATENT DOCUMENTS

| | | | |
|---|---|---|---|
| 4,293,757 A | 10/1981 | Niemi |
| 4,309,774 A | 1/1982 | Guzowski |
| 4,365,627 A | 12/1982 | Wing |
| 4,455,881 A | 6/1984 | Clark |
| 4,721,517 A | 1/1988 | Cloutier |
| 4,848,166 A | 7/1989 | Pannwitz |
| 4,961,916 A | 10/1990 | Lesage |
| 5,029,342 A | 7/1991 | Stein |
| 5,031,237 A | 7/1991 | Honrud |
| 5,056,355 A | 10/1991 | Hepher |
| 5,561,855 A | 10/1996 | McFall |
| 5,651,810 A | 7/1997 | Flaherty |
| 7,178,932 B1 | 2/2007 | Buckman |
| 7,534,005 B1 | 5/2009 | Buckman |
| 7,658,891 B1 | 2/2010 | Barnes |
| 7,810,492 B2 | 10/2010 | Church |
| 7,926,118 B2 | 4/2011 | Becker |
| 7,934,846 B1 | 5/2011 | Schwanz |
| 8,607,784 B2 | 12/2013 | Tilley |
| 9,271,872 B2 | 3/2016 | Becker |
| 2002/0056458 A1 | 5/2002 | Evonitz |
| 2002/0184957 A1 | 12/2002 | Kuhn |
| 2002/0190866 A1 | 12/2002 | Richardson |
| 2003/0058097 A1 | 3/2003 | Saltzstein |
| 2005/0002083 A1 | 1/2005 | Fergason |
| 2005/0041531 A1 | 2/2005 | Sekura |
| 2008/0189820 A1 | 8/2008 | Duffy |
| 2009/0055987 A1 | 3/2009 | Becker |
| 2009/0065489 A1 | 3/2009 | Duffy |
| 2009/0081804 A1 | 3/2009 | Tuchman |
| 2009/0210989 A1 | 8/2009 | Becker |
| 2009/0235439 A1 | 9/2009 | Cox |
| 2010/0224610 A1 | 9/2010 | Wallace |
| 2010/0231394 A1 | 9/2010 | Finchum |
| 2012/0138051 A1 | 6/2012 | Curran |
| 2012/0260918 A1 | 10/2012 | Sayers |
| 2012/0286958 A1 | 11/2012 | Dunbar |
| 2013/0092164 A1 | 4/2013 | Curran |
| 2014/0166001 A1 | 6/2014 | Kooken |
| 2014/0376211 A1 | 12/2014 | Robinson |
| 2016/0271428 A1 | 9/2016 | Ehler |
| 2016/0297025 A1 | 10/2016 | Enyedy |
| 2017/0013904 A1 | 1/2017 | Chantry et al. |

FOREIGN PATENT DOCUMENTS

| | | |
|---|---|---|
| CN | 205251827 U | 5/2016 |
| DE | 20 2013 101 085 U1 | 3/2013 |
| GB | 1 308 532 A | 2/1973 |
| GB | 2 032 284 B | 5/1980 |
| JP | 53-117532 A | 10/1978 |
| JP | 53-117532 B | 9/1987 |
| JP | H11-42247 A | 2/1999 |
| JP | 008-516779 A | 5/2008 |
| JP | 2009-507645 A | 2/2009 |
| JP | 2010-067244 A | 3/2010 |
| WO | 2007/029033 A1 | 3/2007 |
| WO | 2007/149556 A1 | 12/2007 |
| WO | 2015/036652 A1 | 3/2015 |
| WO | 2015/061186 A1 | 4/2015 |
| WO | 2016/001651 A1 | 1/2016 |

OTHER PUBLICATIONS

Optrel Expert E680 Auto-Darkening Welding Helmet w e3000 PAPR Systemby USA Weld (www.usaweld.com/Optrel-Expert-E680-w-PAPR-System-p/4550.100.htm) Accessed on Mar. 30, 2017—3 pages.
PAPR with Titanium 9400 Helmet by Miller Electric Mfg_ Co. (www.millerwelds.com/safety/respiratory/powered-air-purifying-respirators-m00482) Accessed on Mar. 30, 2017—4 pages.
VIKING™ PAPR 3350 Welding Helmet by the Lincoln Electric Company/Lincoln Global, Inc. (www.lincolnelectric.com/assets/global/Products/K3930-1/e14744.pdf). May 2015—8 pages.
PAPR Ventilated Welding Helmet System by Princess Auto Ltd. (www.princessauto.com/en/detail/pro-point-papr-ventilated-welding-helmet-system/A-p8613119e) Accessed on Mar. 30, 2017—6 pages.
Jackson Safety AirmaxPowered Air Purifying Respirator by Thomas Publishing Company (news.thomasnet.com/companystory/two-kimberly-clark-professional-products-recognized-for-excellence-20056126) Accessed on Apr. 11, 2017—5 pages.
HYDRA Powered Respirator by Helmet Integrated Systems Ltd (www.helmets.co.uk/industrial-respiratory/pureflonydra) Accessed on Mar. 30, 2017—3 pages.
HYDRA Powered Respirator by Helmet Integrated Systems Ltd—Oct. 2015—2 pages.
PureFlow HYDRA PAPR System, Technical Data Sheet by Helmet Integrated Systems Ltd—Sep. 2015—1 page.
Speedglas Welding Helmet 9100 FX Air by Dragon Industrial Welding & Industrial Supplies (www.dragonindustrial.com.au/products/welding/speedglas-welding-helmet-9100-fx-air/) Accessed Mar. 30, 2017—2 pages.
Written Opinion for Corresponding Application No. PCT/FI2014/050692 dated Dec. 17, 2014.
International Preliminary Report on Patentability for Corresponding Application No. PCT/FI2014/050692 dated Sep. 4, 2015.
International Search Report for Corresponding Application No. PCT/FI2014/050692 dated Dec. 17, 2014.
Liu, et al., Welding Helmet Airborne Fume Concentrations Compared to Personal Breathing Zone Sampling, Mar. 1995, American Industrial Hygiene Association Journal), 56(3): 280-3, in Office action for U.S. Appl. No. 13/106,525 dated Aug. 14, 2013.
Viking 3350 PAPR Powered Air Purifying Respirator Welding Helmet, Lincoln Electric, available online at: http://www.lincolnelectric.com/en-us/Equipment/welding-gear/Pages/product.aspx?product=K3930-1 (Lincoln Electric), accessed May 5, 2016.
Welding PAPR System, Miller Electric, available online at: https://www.amazon.com/Miller-Electric-Welding-PAPR-System/dp/B007ICNWJE, accessed on May 5, 2016.
Extended European Search Report from Corresponding Application No. EP 17 00 1567; dated Mar. 9, 2018.

WELDING HELMET CONFIGURATION PROVIDING REAL-TIME FUME EXPOSURE WARNING CAPABILITY

CROSS-REFERENCE TO RELATED APPLICATIONS

This application is a continuation-in-part of U.S. patent application Ser. No. 15/281,784, filed on Sep. 30, 2016, which is a continuation-in-part of U.S. patent application Ser. No. 13/106,525, filed on May 12, 2011, the disclosures of which are incorporated herein by reference.

TECHNICAL FIELD

Certain embodiments relate to the monitoring of fumes during a welding process. More particularly, certain embodiments relate to welding helmets, methods, and kits providing real-time fume exposure monitoring and warning capability.

BACKGROUND

During a welding process (e.g., an arc welding process), contaminants such as fumes can be generated which, if breathed in by a welder, can be harmful to the welder. In many welding situations (especially indoor situations), ventilation equipment is used to draw up and vent away the fumes. However, sometimes the ventilation equipment may be inadequate for a particular welding process or scenario, or the ventilation equipment may not be properly set up or properly used by the welder. Because safety and health regulations tend to be performance based, compliance with industrial hygiene standards is dependent upon having actual workplace exposure determinations made by a qualified industrial hygienist. Current practice is to perform a full shift monitoring where a sampling device is placed on the worker to filter and collect a representative sample of the contaminants present in the worker's breathing zone. The goal is to obtain an eight hour time-weighted average concentration which may then be compared with the allowable levels in the regulations. However, many times, results cannot be obtained until several weeks after the sampling event as it is often necessary to send the samples to an accredited lab for analysis.

Further limitations and disadvantages of conventional, traditional, and proposed approaches will become apparent to one of skill in the art, through comparison of such approaches with embodiments of the present invention as set forth in the remainder of the present application with reference to the drawings.

SUMMARY

Welding helmets, systems, and kits providing real-time fume exposure monitoring and warning capability during an arc welding process are disclosed herein. A welding helmet configured to protect the head of a user during a welding process is configured with an intelligent warning apparatus and an air-sampling pick-up and output port. The air-sampling pick-up and output port connects to a proximal end of an air sampling tube for sampling breathable air within the welding helmet, and a distal end of the air sampling tube connects to an air-sampling in-take port of an external aerosol monitoring device. The intelligent warning apparatus communicates with the aerosol monitoring device to receive air sample output data from the aerosol monitoring device, and to process the air sample output data to generate warning data and/or warning signals based on preset exposure level set points and/or exposure warning operating modes. As a result, a welder and/or, for example, a welder's supervisor can be readily informed of any unacceptable exposure to the welder during the welding process, before any significant harm can occur to the welder. Such helmets, systems, and kits may be used as a powerful day-to-day tool for both managing and more effectively understanding workplace exposures.

These and other features of the claimed invention, as well as details of illustrated embodiments thereof, will be more fully understood from the following description and drawings.

DETAILED DESCRIPTION

Embodiments of the present invention are concerned with welding helmets, systems, and kits providing real-time fume exposure monitoring and warning capability during an arc welding process. In accordance with certain embodiments of the present invention, such capability is provided, at least in part, in a welding helmet worn by the user performing the welding process.

As used herein, the term "integrated" refers to being positioned on, being a physically integral part of, or being attached to (with or without the capability to be subsequently unattached). As used herein, the term "real-time" refers to the monitoring, communication, and processing of air sample output data during a welding process such that a welder and/or, for example, a welder's supervisor can be readily informed of any unacceptable exposure to the welder during the welding process, before any significant harm can occur to the welder. As used herein, the term "aerosol" means a system of particles dispersed in a gas (e.g., solid fume or smoke particles dispersed in air).

Figure 1:
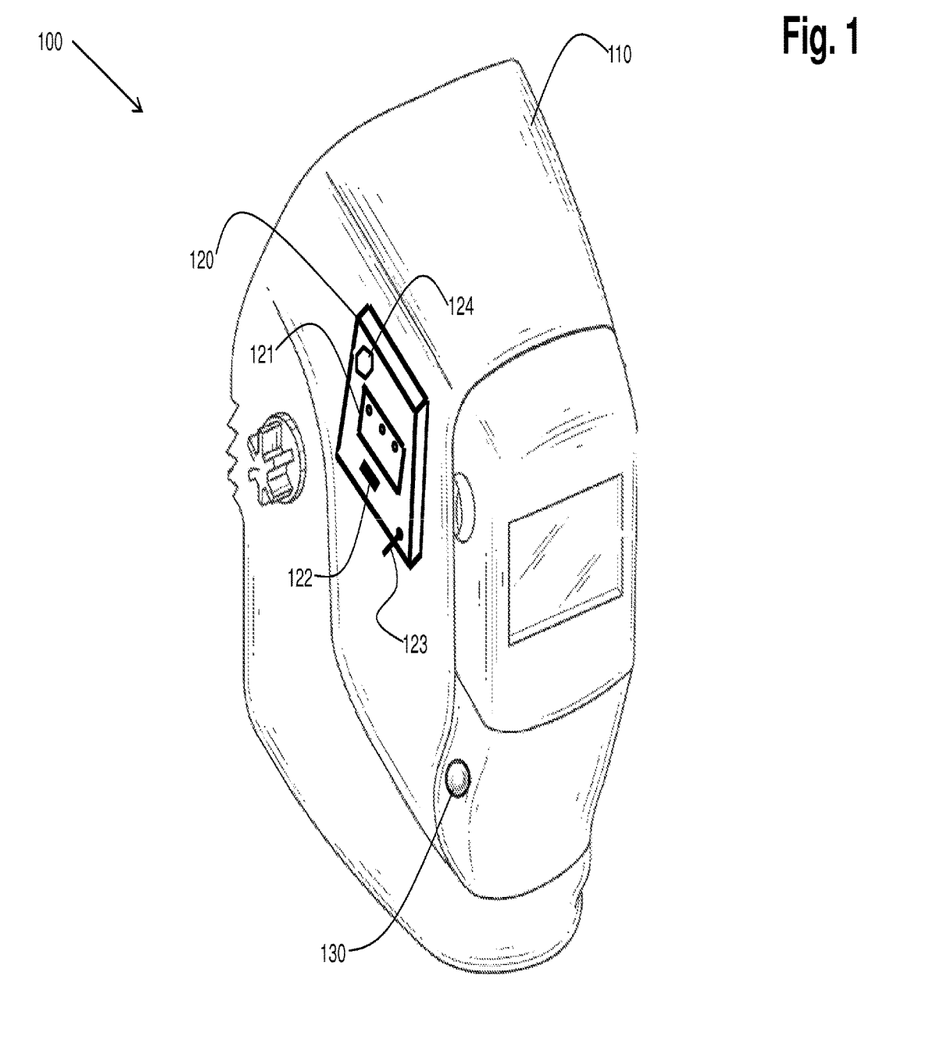
FIG. 1 is an illustration of a first example embodiment of a welding helmet for providing real-time fume exposure warning capability during a welding process.

Details of various embodiments of the present invention are described below herein with respect to FIGS. 1-6. FIG. 1 is an illustration of a first example embodiment of a welding helmet 100 for providing real-time fume exposure warning capability during a welding process. The welding helmet 100 includes a welding headgear 110 configured to be worn on the head of a welder to protect the welder during a welding process. The welding helmet 100 also includes an intelligent warning apparatus (IWA) 120 integrated with the welding headgear 110. The IWA 120 is configured to communicatively interface with an external aerosol monitoring (EAM) device to receive air sample output data from the EAM device. The IWA 120 generates warning information and other environmental status information in response to receiving the air sample output data from the EAM device. Details of the interaction of the IWA 120 and the EAM device are described later herein.

In the embodiment of FIG. 1, the IWA 120 is positioned on the outside of the helmet 110. In accordance with certain embodiments of the present invention, the IWA 120 may be fixed on the welding headgear 110, or may be attachable to and detachable from the welding headgear 110. The IWA 120 includes a user interface 121, a communication input port 122 (e.g., a USB port), a radio frequency (RF) antenna 123, and an alarm or alert device 124. These elements of the IWA 120 are described in more detail later herein. In accordance with an alternative embodiment of the present invention, the alarm device 124 may be separate from the IWA 120 and integrated elsewhere on or within the helmet 100. In such an alternative embodiment, the IWA 120 would activate the alarm device 124 in a wired or wireless manner.

The welding helmet 100 further includes an air-sampling pick-up and output port (ASPOP) 130 integrated with the welding headgear 110. The ASPOP 130 is configured to sample or collect breathable air within the welding headgear 110 and to connect to a proximal end of an air sampling tube for funneling the sampled air away from the headgear 110. A distal end of the air sampling tube is attached to an EAM device as discussed later herein. As used herein, the term "breathable air" means a sample of air that is representative of the air being breathed by the welder while wearing the helmet 100. Even though the ASPOP 130 is shown near the front of the welding headgear 110 in FIG. 1, the ASPOP 130 may be located almost anywhere on the welding headgear 110 (e.g., toward the back of the welding headgear 110).

Figure 2:
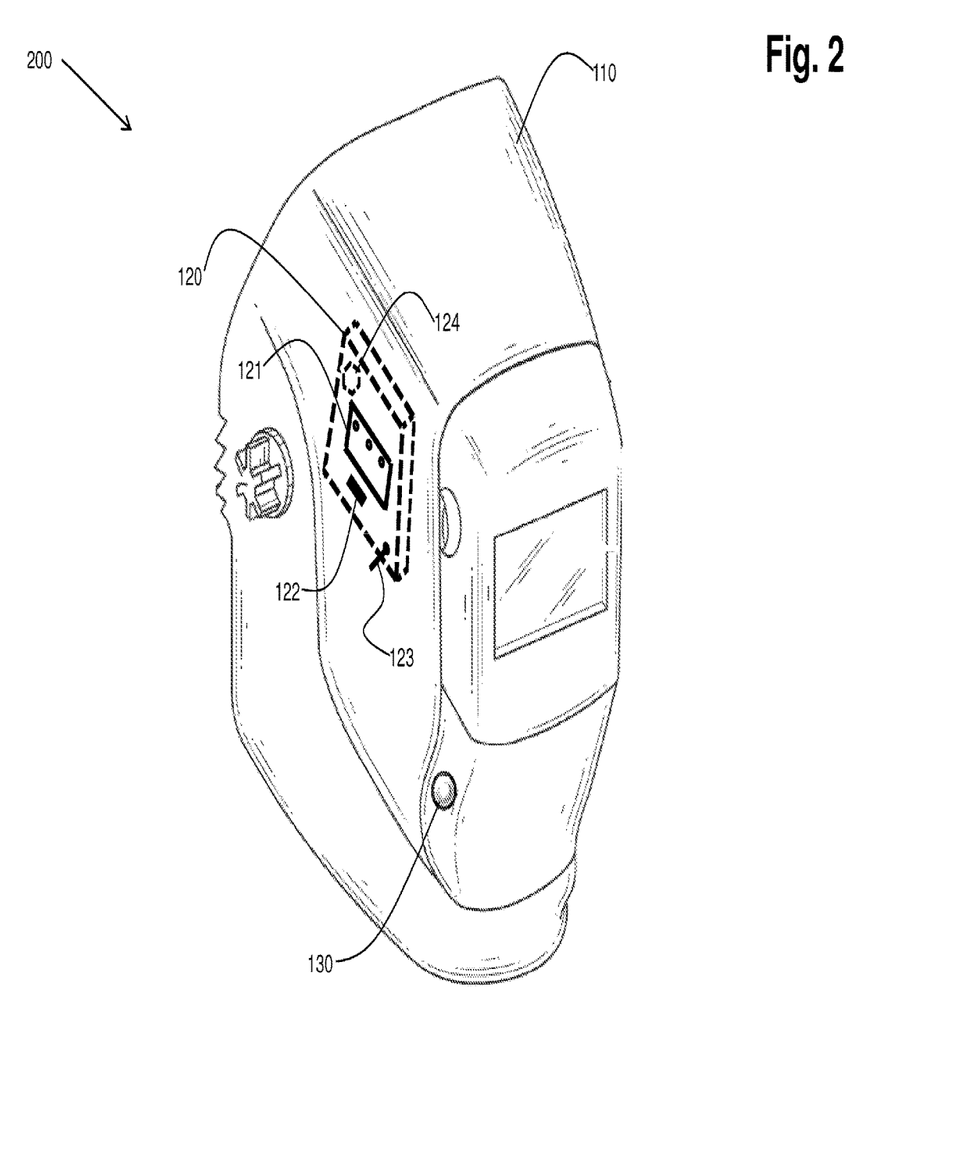
FIG. 2 is an illustration of a second example embodiment of a welding helmet for providing real-time fume exposure warning capability during a welding process.

FIG. 2 is an illustration of a second example embodiment of a welding helmet 200 for providing real-time fume exposure warning capability during a welding process. The welding helmet 200 of FIG. 2 is similar to the welding helmet 100 of FIG. 1. However, the welding helmet 200 includes an IWA 120 that is largely integrated on the inside of the welding headgear 110, as indicated by the dashed lines of the IWA 120 in FIG. 2. However, the user interface 121, the communication input port 122, and the RF antenna 123 are still accessible from the outside of the welding headgear 110. The alarm or alert device 124 is on the inside of the welding headgear 110. In the embodiment of FIG. 2, much of the IWA 120 is protected by being integrated inside the welding headgear 110.

Figure 3:
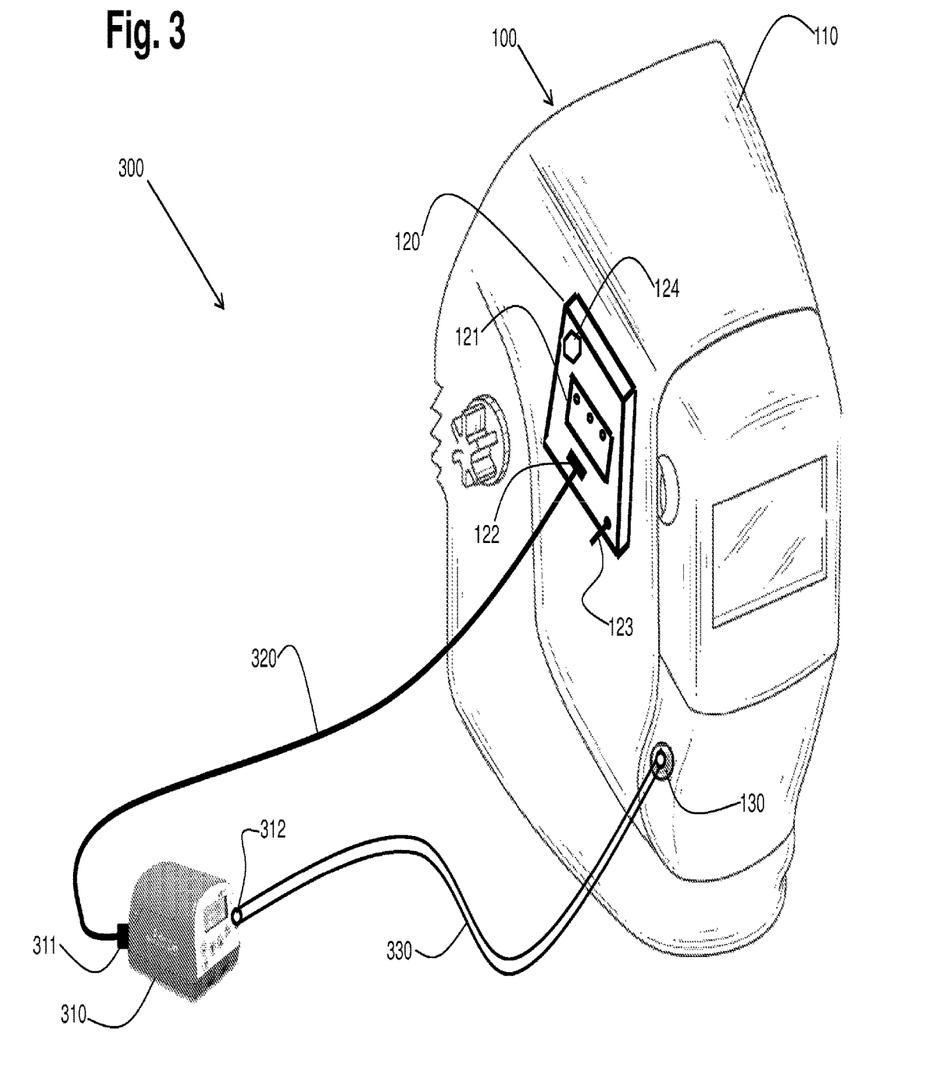
FIG. 3 is an illustration of a first embodiment of a system for providing real-time fume exposure monitoring and warning capability using the welding helmet of FIG. 1 (or, alternatively, the welding helmet of FIG. 2) during a welding process.

FIG. 3 is an illustration of a first embodiment of a system 300 for providing real-time fume exposure monitoring and warning capability using the welding helmet 100 of FIG. 1 (or, alternatively, the welding helmet 200 of FIG. 2) during a welding process. In addition to the welding helmet 100, the system 300 includes an external aerosol monitoring (EAM) device 310 that is external to the helmet 100. The EAM device 310 is configured to determine the concentration of one or more contaminants in the sampled breathable air and generate associated air sample output data. For example, the EAM device 310 may be a laser photometer device. Examples of such laser photometer devices are the SIDE-PAK™ devices as manufactured by TSI, Inc. The system 300 may further include a belt or harness (not shown) for holding the EAM device 310 while the belt or harness is worn by the user.

The system 300 also includes a communication cable 320 (e.g., a USB cable) connecting the communication input port 122 of the IWA 120 with a data output port 311 of the EAM device 310. During operation, the EAM device 310 sends air sample output data to the IWA 120 via the communication cable 320. Both the EAM device 310 and the IWA 120 may be powered by a battery or a re-chargeable power pack, for example. Alternatively, the EAM device 310 and/or the IWA 120 may be powered by, for example, an AC adapter that plugs into an electrical outlet, or by an auxiliary power source of a welding power source or wire feeder.

The system 300 further includes an air-sampling tube 330. The air-sampling tube 330 may be a durable, heat-resistant, flexible plastic tube, in accordance with an embodiment of the present invention. One end of the tube 330 connects to the ASPOP 130 on the helmet 100. The other end of the tube 330 connects to the air-sampling in-take port 312 on the EAM device 310. The EAM device 310 includes a pump (not shown) to create a vacuum which draws breathable air from within the helmet 100 through the ASPOP 130, through the tube 330, through the air-sampling in-take port 312, and into the EAM device 310 for analysis. In accordance with an embodiment of the present invention, the communication cable 320 and the air-sampling tube 330 are run together as one harness to provide a "clean" design implementation. In such an embodiment, the air-sampling in-take port 312 and the data output port 311 may be relatively close together on the EAM device 310. Similarly, the communication input port 122 and the ASPOP 130 may be relatively close together on the headgear 110.

During operation of the system 300, as the EAM device 310 draws in breathable air from the helmet 100, the EAM device 310 analyzes the sampled breathable air to determine particle mass concentration (e.g., via aerosol counting) in the sampled air. In accordance with an embodiment of the present invention, the EAM device 310 is a laser photometer device capable of determining real-time aerosol mass concentration and time-weighted average (TWA) aerosol mass concentration over longer periods of time, and is capable of discriminating between various ranges of particle size.

The mass concentrations determined by the EAM device 310 are sent, via the communication cable 320, to the IWA 120 as air sample output data for processing and analysis. Other forms or types of air sample output data may be generated by the EAM 310 and sent to the IWA 120 as well, in accordance with various embodiments of the present invention. For example, the EAM device 310 may also generate and log historical exposure data over time, or even over multiple welding process sessions.

The various elements of the system 300 of FIG. 3 (welding helmet, EAM device, IWA, air-sampling tube, communication cable, and harness) may be provided in the form of a kit which can be easily and readily assembled by a user for use, and subsequently disassembled after use.

Figure 4:
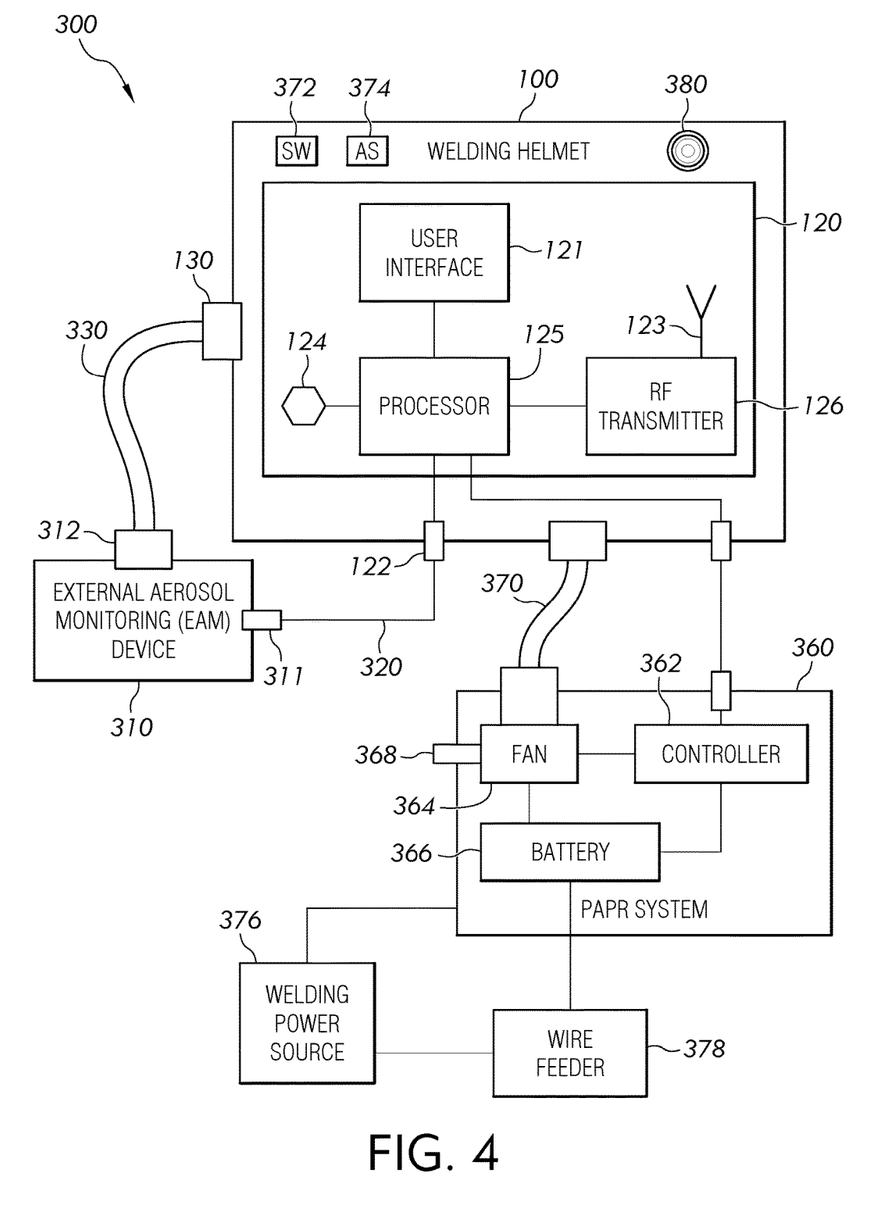
FIG. 4 is a functional block diagram of the system of FIG. 3 showing functional elements of a first embodiment of the intelligent warning apparatus (IWA) of the welding helmet of FIG. 1 (or the welding helmet 200 of FIG. 2)

FIG. 4 is a functional block diagram of the system 300 of FIG. 3 showing functional elements of a first embodiment of the IWA 120 of the welding helmet 100 of FIG. 1 (or the welding helmet 200 of FIG. 2). As seen in FIG. 4, the IWA 120 includes a processor 125 and an RF transmitter 126 connected to the RF antenna 123. The processor 125 is operatively connected to the RF transmitter 126, the user interface 121, and the alarm or alert device 124. In accordance with various embodiments of the present invention, the processor 125 may be a software programmable microprocessor, a digital signal processor, a microcontroller, or any other processing device or chip capable of being configured or programmed to provide the processing functionality described herein for the processor 125. The processor 125 also operatively interfaces to the EAM device 310 via the communication cable 320 to receive air sample output data.

The processor 125 processes the air sample output data and generates exposure warning data and information. The exposure warning data and information may include alert data indicating when certain pre-defined exposure level limits are being exceeded, as well as other data and information including, for example, contaminant concentration level history and running time-averaged data.

The user interface 121 may be a touch-sensitive display or a configuration of switches and/or buttons, for example. Other types of user interfaces are possible as well. In one embodiment, the user interface is used by the welder to set one or more exposure level set points. An exposure level set point is a value that gets compared to the air sample output data (or a processed version thereof) by the processor 125. The air sample output data is representative of a concentration of one or more contaminants in the sampled breathable air. A user may rely on a standard maximum fume exposure guideline (MFEG) to determine an appropriate exposure level set point for a particular welding process, for example.

If the processor 125 determines that a concentration of a contaminant has been exceeded (i.e., determines that a warning condition has occurred), then the processor 124 may generate a warning signal to activate the alarm device 124 to alert the user of the situation. The alarm device 124 may be an audible alarm device, a visual alarm device, or a combination of the two, in accordance with various embodiments of the present invention. Other types of alarm devices are possible as well such as, for example, a vibrating alarm device. In accordance with an alternative embodiment of the present invention, the alarm device 124 may be separate from the helmet 100 and may be wirelessly activated by the IWA 120 of the helmet 100. Furthermore, if the welding helmet is of a type having an internal display that may be viewed by the welder, warning information from the IWA 120 may be displayed on the internal display.

In another embodiment, the user interface is used by the welder to select a predefined warning operating mode. A pre-defined warning operating mode is a mode of operation of the system 300 that is programmed or configured in the processor 125 which correlates to a particular welding process and the likely contaminants that may be produced as part of the that particular welding process. A particular pre-defined warning operating mode includes preset exposure level set points and possibly other parameters and/or operating algorithms corresponding to the particular welding process. A predefined warning operating mode is designed to keep the welder informed (e.g., via alerts) and safe with respect to contaminant exposure during that particular welding process.

In accordance with an embodiment of the present invention, the RF transmitter 126 receives warning data and information from the processor 125 and transmits the warning data and information to an external warning station (not shown). The external warning station may be, for example, a personal computer running an exposure software application in an office just outside a welding work environment in a factory. The external warning station may be manned by a welding supervisor to keep track of exposure levels of one or more welders currently working in the welding work environment.

In accordance with another embodiment of the present invention, the RF transmitter 126 receives warning data and information from the processor 125 and transmits associated command messages or signals to a welding power source 376 currently being operated by a user of the system 300 to turn off or shut down the welding power source, for example, when the processor determines that contaminant levels are unsafe or are approaching unsafe levels. Similarly, the RF transmitter 126 may transmit associated command messages or signals to a ventilation system to change an operating state of the ventilation system (e.g., to increase a fan speed of the ventilation system) if the processor determines that contaminant levels are unsafe or are approaching unsafe levels.

The ventilation system may be one for an entire work environment (e.g., a factory or room therein), or may be specific to an individual welder (e.g., a powered air purifying respirator (PAPR) 360 attached to the welding helmet 100). For purposes of illustration, a hard-wired PAPR system 360 is illustrated schematically in FIG. 4. As illustrated, the PAPR system 360 includes a controller 362, fan 364, and battery 366. That fan 364 draws air in through an intake 368 and expels the air through a hose 370 connected to the helmet 100. The controller 362 is operatively connected to the fan 364 to control operation (e.g., a speed) of the fan 364 based on a received input. In the embodiment of FIG. 4, the input is received from a hardwired connection from the processor 125 of the IWA 120. The battery 366 serves to power the fan 368 and controller 362.

For a large scale ventilation system, the RF transmitter 126 may transmit command messages or signals to a controller for the ventilation system to automatically alter a fan speed or other property of the ventilation system. Similarly, the RF transmitter 126 may transmit command messages or signals to a controller 362 for the PAPR system 360 to automatically alter a fan speed or other property of the PAPR system 360. For PAPR systems 360 that are located on or near a user and/or connected to the welding helmet 100, the use of an RF transmitter 126 for communicating with the PAPR system 360 (RF receiver/transceiver of PAPR system 360 not illustrated) may be replaced by a hard-wired connection, as is illustrated in FIG. 4.

For either the large scale ventilation or PAPR systems 360, the fan 364 may operate at multiple speeds. For example, a high speed may be used when contaminate exposure is above a threshold and a low speed may be used when contaminate exposure is below the threshold. Therefore, based on the exposure information generated by the processor 125 of the IWA 120, the processor 125 may determine whether to send a signal to increase or decrease the fan speed to an appropriate level for the determined exposure. The threshold used for determining the fan speed may be different than that used for determining an alarm condition, and the processor may utilize respective different thresholds for different types of airborne contaminants. The thresholds may be set at the user interface 121 of the IWA 120. The user interface 121 of the IWA 120 may also serve as a user interface of the ventilation system, thereby allowing direct control of the fan or other properties of the system from the IWA 120.

For PAPR systems 360, the fan 364 is often powered by a battery 366 or other limited power source. Thus, controlling the fan speed to an appropriate level based on a determined exposure results in more efficient power consumption. For example, when exposure is low the fan does not need to operate at a high speed and, therefore, power consumption can be reduced by maintaining the fan at the low speed.

While the state of the ventilation or PAPR systems may be altered by changing the fan speed, any other properties of the systems may be changed in a similar manner so as to increase the system's efficiency.

The PAPR fan 364 can be manually activated, such as by a switch on the PAPR system 360. The PAPR system 360 can also be configured to automatically activate the fan 364. For example, the PAPR fan 364 can be automatically activated when the welding helmet 100 or headgear is moved from a raised position (in which the helmet does not cover a user's face) to a lowered position for protection during welding. The PAPR fan 364 can also be automatically deactivated when the helmet 100 or headgear is moved from the lowered position to the raised position. The welding helmet 100 can include a position switch 372 or other sensor for determining movements of the helmet between the raised and lowered positions. The position switch 372 can provide a signal to the processor 125 in the IWA 120, or another processor in the welding helmet 100, which is communicatively coupled to the controller 362 in the PAPR system 360, to inform the PAPR system of the current position of the welding helmet 100. Based on the current position of the welding helmet 100, the controller 362 in the PAPR system 360 can automatically activate or deactivate the fan 364, so that the fan is operated only when necessary.

Similar to the position switch 372, the welding helmet 100 can include an arc sensor 374 for activating the PAPR fan 364. When an arc welding operation begins and an arc is struck between a welding torch and workpiece, the arc sensor 374 will generate a signal that can be communicated to the controller 362 in the PAPR system 360. When an arc is detected, the controller 362 can automatically activate the PAPR fan 364 if it is not already running. The PAPR fan 364 can be deactivated when the arc is no longer sensed by the arc sensor 374, or the fan can be maintained in a running state until manually switched off or the welding helmet 100 is raised.

At least one of the welding helmet 100, the IWA 120, the EAM 310, and the PAPR system 360 can communicatively interface with the welding power source 376 and/or a wire feeder 378. The welding power source 376 generates welding waveforms for performing a welding operation, and the wire feeder 378 feeds a consumable welding electrode to a welding torch (not shown) used to perform the welding operation. In certain embodiments, the welding power source 376 or wire feeder 378 can inform the PAPR system 360 (or a device in communication with the PAPR system, such as the IWA 120) that a torch trigger signal has been received by the welding power source from a welding torch. Similar to fan operations based on the arc sensor 374, the PAPR system 360 can automatically activate the fan 364 when the torch trigger signal is received by the welding power source.

The wire feeder 378 will typically be located near the operator and, thus, also near to the PAPR system 360. In certain embodiments, the PAPR system 360 can be operatively connected to the wire feeder 378 to charge the PAPR battery 366 by the wire feeder. The wire feeder 378 can include a charging output for supplying charging power and providing a suitable electrical connection to the PAPR system 360.

The welding helmet 100 can include a camera 380 for capturing images of a welding environment. In certain embodiments, the camera 380 can be part of an augmented reality welding system built into the welding helmet 100. The processor 124 in the IWA 120 or another processor in the welding helmet 100 can receive images captured by the camera 380 and analyze the images to determine the presence or absence of fumes during a welding operation. Based on the presence, quantity or other characteristic of fumes in the captured images, the PAPR system 360 can be signaled to increase or decrease fan speed to an appropriate level.

Operations of the welding power source 376 can be controlled based on the air sample output data from the EAM 310 or the presence of fumes in the images captured by the camera 380. For example, the welding power (e.g., current or voltage) can be reduced based on fume or contaminant level, or the welding power source 376 can be commanded to stop the welding operation. Operations of the welding power source 376 can also be controlled based on the charge level of the battery 366 in the PAPR system 360. For example, the welding power source 376 can be commanded to stop the welding operation when the charge level of the battery 366 drops below a predetermined level. The stop command can come from directly from the PAPR system 360 or another device, such as the IWA 120, or the battery charge level can be communicated to the welding power source 376 for comparison to the predetermined level by the welding power source.

In accordance with other embodiments of the present invention, the RF transmitter 126 may be replaced with some other type of wireless communication device such as, for example, an infrared transmitter or a sonic transmitter. Other types of wireless communication devices may be possible as well. Accordingly, the external warning station, the welding power source, and the ventilation system would be configured to communicate with such an alternative wireless communication device.

Figure 5:
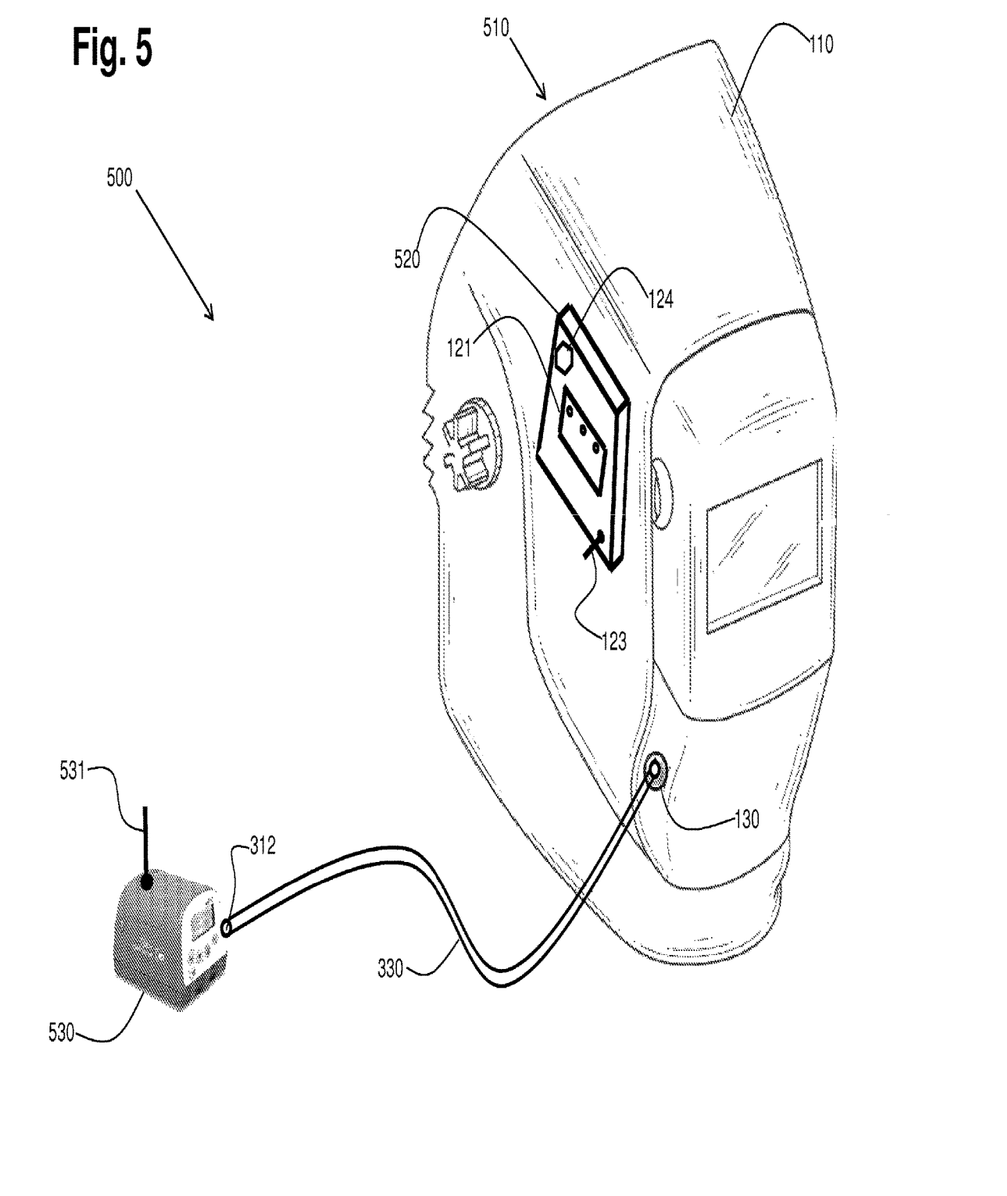
FIG. 5 is an illustration of a second embodiment of a system for providing real-time fume exposure monitoring and warning capability using a slightly modified embodiment of a welding helmet during a welding process.

FIG. 5 is an illustration of a second embodiment of a system 500 for providing real-time fume exposure monitoring and warning capability using a slightly modified embodiment of a welding helmet 510 during a welding process. In the system 500 of FIG. 5, communication between a second embodiment of an EAM device and a second embodiment of an IWA is performed via wireless means. The EAM device 530 of FIG. 5 does not have a data output port 311 but, instead, has an RF antenna 531 for transmitting air sample output data to the IWA 520 of FIG. 5. Similarly, the IWA 520 of FIG. 5 does not have a communication input port 122 but, instead, has the RF antenna 123 for receiving air sample output data from the EAM device 530. In accordance with alternative embodiments of the present invention, other wireless means of communicating air sample output data from the EAM device to the IWA may include infrared means, sonic means, or some other wireless means.

Figure 6:
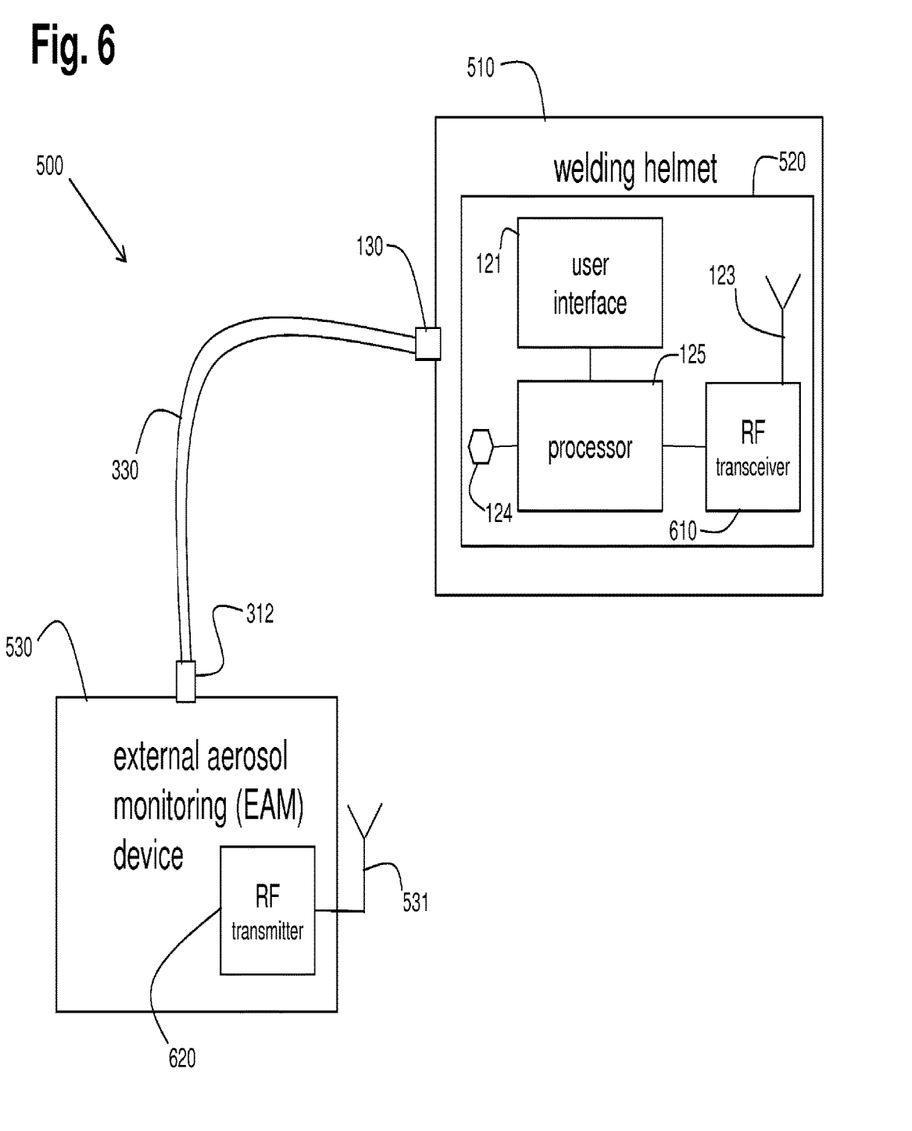
FIG. 6 is a functional block diagram of the system of FIG. 5 showing the functional elements of the IWA of the welding helmet of FIG. 5.

FIG. 6 is a functional block diagram of the system 500 of FIG. 5 showing the functional elements of the IWA 520 of the welding helmet 510 of FIG. 5. The EAM device 530 includes an RF transmitter 620 operatively connected to the RF antenna 531. The RF transmitter 620 functions to transmit air sample output data via the RF antenna 531 to the IWA 520. The IWA 520, instead of having an RF transmitter 126, has an RF transceiver 610 which functions to receive air sample output data via the RF antenna 123 and pass the air sample output data to the processor 125 for processing and analysis.

Also, the RF transceiver 610 functions to receive warning data and information from the processor 125 and transmit the warning data and information to an external warning station (not shown). The external warning station may be, for example, a mobile device running an exposure software application. The external warning station may be worn by an industrial hygienist inspecting a welding work environment in a factory to determine if exposure levels experienced by one or more welders currently working in the welding work environment meets current industrial standards.

Furthermore, the RF transceiver 610 may function to receive warning data and information from the processor 125 and transmit associated command messages or signals to a welding power source (not shown) currently being operated by a user of the system 500 to turn off or shut down the welding power source, for example, when the processor 125 determines that contaminant levels are unsafe or are approaching unsafe levels. Similarly, the RF transceiver 610 may transmit associated command messages or signals to a ventilation system (not shown) to change an operating state of the ventilation system, as described above, (e.g., to increase a fan speed of the ventilation system) if the processor 125 determines that contaminant levels are unsafe or are approaching unsafe levels. In accordance with other embodiments of the present invention, the RF transceiver 610 may be replaced with some other type of wireless communication device such as, for example, an infrared transceiver or a sonic transceiver. Other types of wireless communication devices may be possible as well. Accordingly, the external warning station, the welding power source, and the ventilation system would be configured to communicate with such an alternative wireless communication device.

In accordance with an embodiment of the present invention, the IWA is configured to generate and/or analyze historical exposure data. For example, the IWA may receive historical exposure data as a form of air sample output data from the EAM device and process and analyze the historical exposure data to generate statistical 531 to the IWA 520. The IWA 520, instead of having an RF transmitter 126, has an RF transceiver 610 which functions to receive air sample output data via the RF antenna 123 and pass the air sample output data to the processor 125 for processing and analysis.

Also, the RF transceiver 610 functions to receive warning data and information from the processor 125 and transmit the warning data and information to an external warning station (not shown). The external warning station may be, for example, a mobile device running an exposure software application. The external warning station may be worn by an industrial hygienist inspecting a welding work environment in a factory to determine if exposure levels experienced by one or more welders currently working in the welding work environment meets current industrial standards.

Furthermore, the RF transceiver 610 may function to receive warning data and information from the processor 125 and transmit associated command messages or signals to a welding power source (not shown) currently being operated by a user of the system 500 to turn off or shut down the welding power source, for example, when the processor 125 determines that contaminant levels are unsafe or are approaching unsafe levels. Similarly, the RF transceiver 610 may transmit associated command messages or signals to a ventilation system (not shown) to change an operating state of the ventilation system (e.g., to increase a fan speed of the ventilation system) if the processor 125 determines that contaminant levels are unsafe or are approaching unsafe levels.

In accordance with other embodiments of the present invention, the RF transceiver 610 may be replaced with some other type of wireless communication device such as, for example, an infrared transceiver or a sonic transceiver. Other types of wireless communication devices may be possible as well. Accordingly, the external warning station, the welding power source, and the ventilation system would be configured to communicate with such an alternative wireless communication device.

In accordance with an embodiment of the present invention, the IWA is configured to generate and/or analyze historical exposure data. For example, the IWA may receive historical exposure data as a form of air sample output data from the EAM device and process and analyze the historical exposure data to generate statistical exposure parameters and trend data as a form of exposure warning data and information. Such statistical exposure parameters and trend data may provide great insight to an industrial hygienist with respect to the environmental operation of a plant or factory (e.g., over a full eight-hour shift, or over an entire week).

In summary, an embodiment of the present invention comprises a welding helmet providing real-time fume exposure warning capability. The welding helmet includes a welding headgear configured to be worn on a head of a user to protect the user during a welding process. The welding helmet further includes an intelligent warning apparatus integrated with the welding headgear and configured to communicatively interface with an external aerosol monitoring device to receive air sample output data from the external aerosol monitoring device. The welding helmet also includes an air-sampling pick-up and output port integrated with the welding headgear and configured to connect to a proximal end of an air sampling tube for sampling breathable air within the welding headgear. A distal end of the air sampling tube is configured to connect to an air-sampling intake port of the external aerosol monitoring device. The intelligent warning apparatus includes a processor configured to process the air sample output data received from the external aerosol monitoring device to generate at least warning data. The intelligent warning apparatus may also include a user interface operatively connected to the processor and configured to allow a user to set at least one exposure level set point and/or to select a warning operating mode from a plurality of pre-defined warning operating modes. The intelligent warning apparatus may further include a wireless communication device operatively connected to the processor and configured to receive at least the warning data from the processor and to wirelessly transmit at least the warning data to an external warning station. The intelligent warning apparatus may also include a wireless communication device operatively connected to the processor and configured to wirelessly receive the air sample output data from the external aerosol monitoring device may be configured to communicatively interface with a welding power source to operatively shut down the welding power source in response to the warning data. The intelligent warning apparatus may further include an alarm device or an alert device operatively connected to the processor and configured to alarm upon reception of a warning signal from the processor. In accordance with an alternative embodiment of the present invention, the alarm or alert device is not part of the intelligent warning apparatus but, instead, operatively interfaces to the intelligent warning apparatus to receive an activating warning signal from the intelligent warning apparatus.

Another embodiment of the present invention comprises, a kit providing real-time welding fume exposure monitoring and warning capability. The kit includes a welding helmet having an air-sampling pick-up and output port integrated therewith. The helmet is configured to be worn on a head of a user of the kit to protect the user during a welding process.

The kit further includes an aerosol monitoring device having an air-sampling intake port and configured to generate air sample output data. The kit also includes an intelligent warning apparatus configured to communicatively interface with the aerosol monitoring device and to generate at least warning data in response to the air sample output data. The intelligent warning apparatus may be physically integrated with the welding helmet, or may be capable of being attached and detached from the welding helmet. The kit further includes an air-sampling tube having a proximal end and a distal end. The air-sampling tube is configured to operatively mate with the air-sampling pickup and output port of the welding helmet at the proximal end of the air-sampling tube, and further configured to operatively mate with the air-sampling intake port of the aerosol monitoring device at the distal end of the air-sampling tube. The kit may further include a communication cable having a proximal end and a distal end. The communication cable is configured to operatively mate with a communication input port of the intelligent warning apparatus at the proximal end of the communication cable. The communication cable is also configured to operatively mate with a data output port of the aerosol monitoring device at the distal end of the communication cable. Alternatively, the communication cable facilitates wired communication from the aerosol monitoring device to the intelligent warning apparatus. The intelligent warning apparatus and the aerosol monitoring device may be configured to wirelessly communicate with each other. The intelligent warning apparatus may include a wireless communication capability configured to transmit warning information generated by the intelligent warning apparatus to an external warning station. The intelligent warning apparatus may be configured to communicatively interface with an external ventilation system to effect a change in an operational state of the external ventilation system in response to the warning data. The intelligent warning apparatus may be configured to communicatively interface with a welding power source to operatively shut down the welding power source in response to the warning data. The intelligent warning apparatus may include a user interface configured to allow a user to set at least one exposure level set point and/or to select a warning operating mode from a plurality of pre-defined warning operating modes. The intelligent warning apparatus may include and alarm device or an alert device configured to be activated when a warning condition is determined by the intelligent warning apparatus. In accordance with an alternative embodiment of the present invention, the alarm or alert device is not part of the intelligent warning apparatus but, instead, operatively interfaces to the intelligent warning apparatus to receive an activating warning condition signal from the intelligent warning apparatus. The kit may further include a harness or belt for holding the aerosol monitoring device while the harness or belt is worn by the user.

A further embodiment of the present invention comprises a system providing real-time fume exposure monitoring and warning capability. The system includes means for protecting a head of a user during a welding process, means for monitoring breathable air samples originating from within the means for protecting to generate air sample output data, and means for processing the air sample output data to generate at least warning data. The system further includes means for communicating the air sample output data from the means for monitoring to the means for processing. The system may also include means for generating an alert or alarm in response to the warning data. The system may further include means for a user to set at least one exposure level setting and means for a user to select a warning operating mode from a plurality of pre-defined warning operating modes. The system may also include means for communicating the warning data to an external warning station, and means for effecting a change in an operational state of an external ventilation system in response to the warning data. The system may further include means for shutting down a welding power source in response to the warning data, and means for holding the means for monitoring on the user.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiments disclosed, but that the claimed subject matter will include all embodiments falling within the scope of the appended claims.

What is claimed is:

1. A helmet system, comprising:
   a welding headgear configured to be worn on a head of a user to protect the user during a welding process; and
   an intelligent warning apparatus integrated with the welding headgear, wherein the intelligent warning apparatus is configured to communicatively interface with an external aerosol monitoring device to receive air sample output data from said external aerosol monitoring device,
   wherein said intelligent warning apparatus includes a user interface operatively connected to a processor and configured to allow a user to select a warning operating mode from a plurality of pre-defined warning operating modes, and wherein said plurality of pre-defined warning operating modes respectively correlate to particular welding processes by including parameter values specific to said particular welding processes.

2. The helmet system of claim 1, further comprising a powered air purifying respirator (PAPR) comprising an air hose connected to the welding headgear and a fan for delivering air through the air hose to the welding headgear.

3. The helmet system of claim 2, wherein the intelligent warning apparatus is configured to communicate with the PAPR and control a fan running speed of the fan.

4. The helmet system of claim 2, wherein the fan automatically activates when the welding headgear is moved from a raised position to a lowered position.

5. The helmet system of claim 2, wherein the fan automatically deactivates when the welding headgear is moved from a lowered position to a raised position.

6. The helmet system of claim 2, wherein the welding headgear comprises and arc sensor, and the fan automatically activates when an arc is detected by the arc sensor.

7. The helmet system of claim 2, wherein the PAPR comprises a battery for powering the fan, and the PAPR is operatively connected to a wire feeder to charge the battery by the wire feeder.

8. The helmet system of claim 2, wherein the helmet system is configured to communicatively interface with a welding power source.

9. The helmet system of claim 8, wherein the PAPR comprises a battery for powering the fan, and the helmet system is configured to transmit a welding stop command to the welding power source based on a charge level of the battery.

10. The helmet system of claim 8, wherein the PAPR comprises a battery for powering the fan, and the helmet system is configured to transmit battery charge level information to the welding power source.

11. The helmet system of claim 8, wherein the helmet system is configured to transmit a power output adjustment command to the welding power source.

12. The helmet system of claim 8, wherein the fan automatically activates based on a torch trigger signal received by the welding power source.

13. A system, comprising:
   a helmet configured to be worn on a head of a user to protect the user;
   an external aerosol monitoring device operatively coupled to the helmet; and
   an intelligent warning apparatus configured to communicatively interface with the external aerosol monitoring device to receive air sample output data from said external aerosol monitoring device,
   wherein said intelligent warning apparatus includes a user interface operatively connected to a processor and configured to allow a user to select a warning operating mode from a plurality of pre-defined warning operating modes, wherein said plurality of pre-defined warning operating modes respectively correlate to particular welding processes by including parameter values specific to said particular welding processes.

14. The system of claim 13, further comprising a powered air purifying respirator (PAPR) comprising an air hose connected to the helmet and a fan for delivering air through the air hose to the helmet.

15. The system of claim 14, wherein the intelligent warning apparatus is configured to communicate with the PAPR and control a fan running speed of the fan.

16. The system of claim 14, wherein the fan automatically activates when the helmet is moved from a raised position to a lowered position.

17. The system of claim 14, wherein the fan automatically deactivates when the helmet is moved from a lowered position to a raised position.

18. The system of claim 14, wherein the helmet comprises and arc sensor, and the fan automatically activates when an arc is detected by the arc sensor.

19. The system of claim 14, further comprising a wire feeder,
   wherein the PAPR comprises a battery for powering the fan, and the PAPR is operatively connected to the wire feeder to charge the battery by the wire feeder.

20. The system of claim 14, further comprising a welding power source, wherein at least one of the helmet, the external aerosol monitoring device, the intelligent warning apparatus, and the PAPR is in communication with the welding power source.

* * * * *